United States Patent [19]

Zeiher

[11] Patent Number: 5,061,267
[45] Date of Patent: Oct. 29, 1991

[54] BALLOON CATHETER FOR RECHANNELING STENOSES IN BODY PASSAGES, IN PARTICULAR OF CORONARY AND PERIPHERAL ARTERIAL VESSELS

[76] Inventor: Andreas Zeiher, Klarastrasse 55, D-7800 Freiburg, Fed. Rep. of Germany

[21] Appl. No.: 393,921

[22] PCT Filed: Dec. 19, 1988

[86] PCT No.: PCT/DE88/00769
§ 371 Date: Aug. 1, 1989
§ 102(e) Date: Aug. 1, 1989

[87] PCT Pub. No.: WO89/05609
PCT Pub. Date: Jun. 29, 1989

[30] Foreign Application Priority Data
Dec. 22, 1987 [DE] Fed. Rep. of Germany ....... 3743578

[51] Int. Cl.[5] .............................................. A61N 5/04
[52] U.S. Cl. ........................................ 606/40; 606/49; 606/194; 128/786; 128/804
[58] Field of Search ........................ 128/784, 786-788, 128/804, 303.13, 394-401, 344; 604/20, 22; 606/27-29, 33, 34, 40, 41, 42, 49, 194

[56] References Cited

U.S. PATENT DOCUMENTS

| | | | |
|---|---|---|---|
| 4,326,529 | 4/1982 | Doss et al. | 606/34 |
| 4,643,186 | 2/1987 | Rosen et al. | 128/784 |
| 4,799,479 | 1/1989 | Spears | 606/194 |
| 4,800,899 | 1/1989 | Elliott | 128/804 |
| 4,807,602 | 2/1989 | Strulet et al. | 606/28 |

Primary Examiner—David Shay
Attorney, Agent, or Firm—Peter C. Richardson; Lawrence C. Akers; Thomas C. Naber

[57] ABSTRACT

A balloon catheter for rechanneling stenoses in body passages, in particular of coronary and peripheral arterial vessels, has a microwave antenna provided in the interior of the balloon, which antenna is connected to a microwave generator by way of a coaxial cable. By action of the microwaves on a microwave-absorbing dilatation liquid and/or a metallic coating on the envelope of the balloon, the catheter is heated and the vessel wall is subjected to thermal aftertreatment to prevent restenosis.

2 Claims, 3 Drawing Sheets

BALLOON CATHETER FOR RECHANNELING STENOSES IN BODY PASSAGES, IN PARTICULAR OF CORONARY AND PERIPHERAL ARTERIAL VESSELS

BACKGROUND OF THE INVENTION

The invention relates to a balloon catheter for rechanneling stenoses in body passages, in particular of coronary and peripheral arterial vessels, with a balloon through which a guide hose guided by a guide wire extends and which is inflatable with a gas or liquid by way of an inflation tube opening into the interior of the balloon.

Balloon catheters for rechanneling stenoses in coronary vessels have been in use by cardiologists for some time, restenosis in 35% of applications being problematic as the chief late complication of the clinically very successful technique. For this reason, it has been proposed to use laser light for thermal aftertreatment of a balloon dilatation with the aid of a light wave guide (The American Journal of Cardiology 56, 953).

European Patent A 2,182,689 describes a balloon catheter for which the tissue surrounding the balloon is heated with laser light fed into the balloon. From the same source, it is known also that an electric heating element may be provided near the distal end of the guide wire, the element being enclosed by the balloon and heating the fluid present in the balloon. The guide hose extending through the balloon is of a diameter only slightly greater than the diameter of the guide wire to avoid the hazard of coagulation of blood penetrating into the guide hose.

From Biomedizinische Technik 32, September 1987 supplement, 33-36, it is known that high-frequency energy may be used to support balloon dilatation. Thus it is proposed that the balloon catheter be provided with a bipolar electrode configuration of two strip electrodes. The strip electrodes are connected to a generator with a frequency of 0.5 to 1 MHz for a period of up to 38 seconds and an output energy of 50 watts maximum. With high-frequency coagulation in the region of the strip electrodes, animal experiments are to ascertain whether a stabilized dilatation can be achieved.

Another device for thermal treatment of the tissue surrounding body cavities with temperature control means is described in U.S. Pat. No. 4,658,836, a direct heating of the body tissue being effected by electromagnetic radiation in the frequency range of radio waves or microwaves.

German Patent 3,011,322 discloses a radiation probe for a device for microwave treatment of body tissue, at the same time permitting application of hyperthermia and radiotherapy, the tissue being irradiated with microwave energy. To concentrate the microwave radiation on the desired tissular region, the radiation probe, capable of being introduced into a body cavity, is fitted out with a coaxial cable whose unshielded end is asymmetrically surrounded in the probe by a bulbous body.

U.S. Pat. No. 4,662,383 describes a balloon catheter for hyperthermia of tumors, charged by way of a supply line with a coolant capable of being drained from the interior of the balloon by way of an outlet line. In the interior of the balloon, a microwave antenna is provided, having a range of radiation extending into the surrounding tissue. Fluids having a low absorption coefficient for microwaves are provided as coolants, in order not to impede penetration of the microwave into the tissue.

SUMMARY OF THE INVENTION

Against the background of the prior art outlined above, the object of the invention is to create a balloon catheter permitting conservative homogeneous heat therapy with a variable and suitably controllable thermal depth of penetration.

In a balloon catheter of the kind mentioned at the outset, this object is accomplished, according to the invention, in that a microwave antenna capable of being connected to a microwave generator by way of a coaxial cable is arranged in the interior of the balloon.

The microwave antenna in the interior of the balloon serves primarily to heat the fluid used to dilate the balloon envelope, said fluid comprising a good liquid absorbent for microwaves, for example a mixture of a common salt solution and a contrast medium containing iodine, to which other substances may be added if desired to enhance the microwave absorption, as for example metal particles suspended in the liquid. The radially symmetrical propagation of the microwaves leads to a homogeneous radially symmetrical heating of the liquid.

To prevent direct penetration of microwaves into the tissue surrounding the balloon catheter, the balloon envelope is preferably provided with a metallic coating. To prevent blood present in the guide hose that traverses the balloon envelope from coagulating when the microwave generator is switched on, the guide hose is capable of being squeezed flat by the pressure of the fluid used for dilatation, so that in such an embodiment the guide hose need not be metalized for shielding, which would interfere with a uniform distribution of microwave energy in the interior of the balloon.

In an expedient embodiment of the invention by way of example, the microwave antenna consists of the anterior end, stripped of its shielding, of a coaxial cable. The arrangement is such that the metallic inner conductor extends along the lengthwise centerline of the inflated balloon, to permit a uniform distance from the balloon wall and hence a uniform thermal treatment.

DETAILED DESCRIPTION OF THE INVENTION

Figure 1:
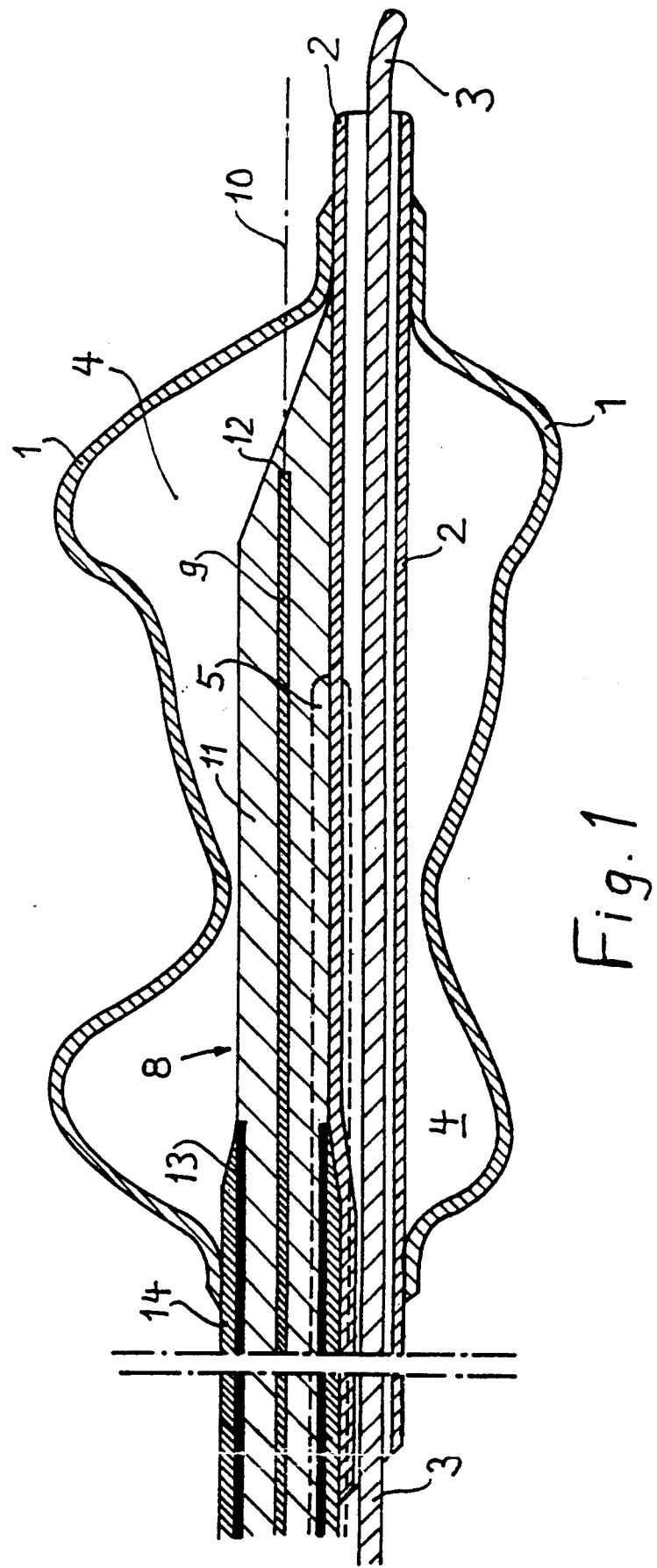

In the following, an embodiment of the invention will be described by way of example with reference to the drawings. In the drawings, FIG. 1 shows a balloon catheter according to the invention in lengthwise section, FIG. 2 shows a balloon catheter according to the invention in inflated condition, partly in section and partly in cut-away perspective, and FIG. 3 shows a cross-section through the midregion of the inflated balloon envelope of the balloon catheter.

In FIG. 1, the balloon catheter for rechanneling stenoses in coronary vessels is represented in lengthwise section. The balloon catheter has a balloon comprising an envelope 1 consisting of a flexible heat-resistant plastic. The envelope 1 is provided on the outside and/or inside with a metallic coating not identified in the drawing. The metallic coating of the balloon consists preferably of a film of gold, silver, chromium, chrome-nickel or copper. The coating may be of uniform thickness throughout, or a fine network with interruptions, for example in the form of stripes. The coating serves to shield against microwaves generated in the envelope 1 to the outside, and as a heating surface heated by microwave absorption.

The envelope 1 encloses a flexibly compressible guide hose 2, which, depending on the construction of the balloon catheter, is only slightly longer than the envelope. The guide hose 2 serves to guide the balloon catheter along a guide wire 3 advanced into the field of operation.

Figure 2:
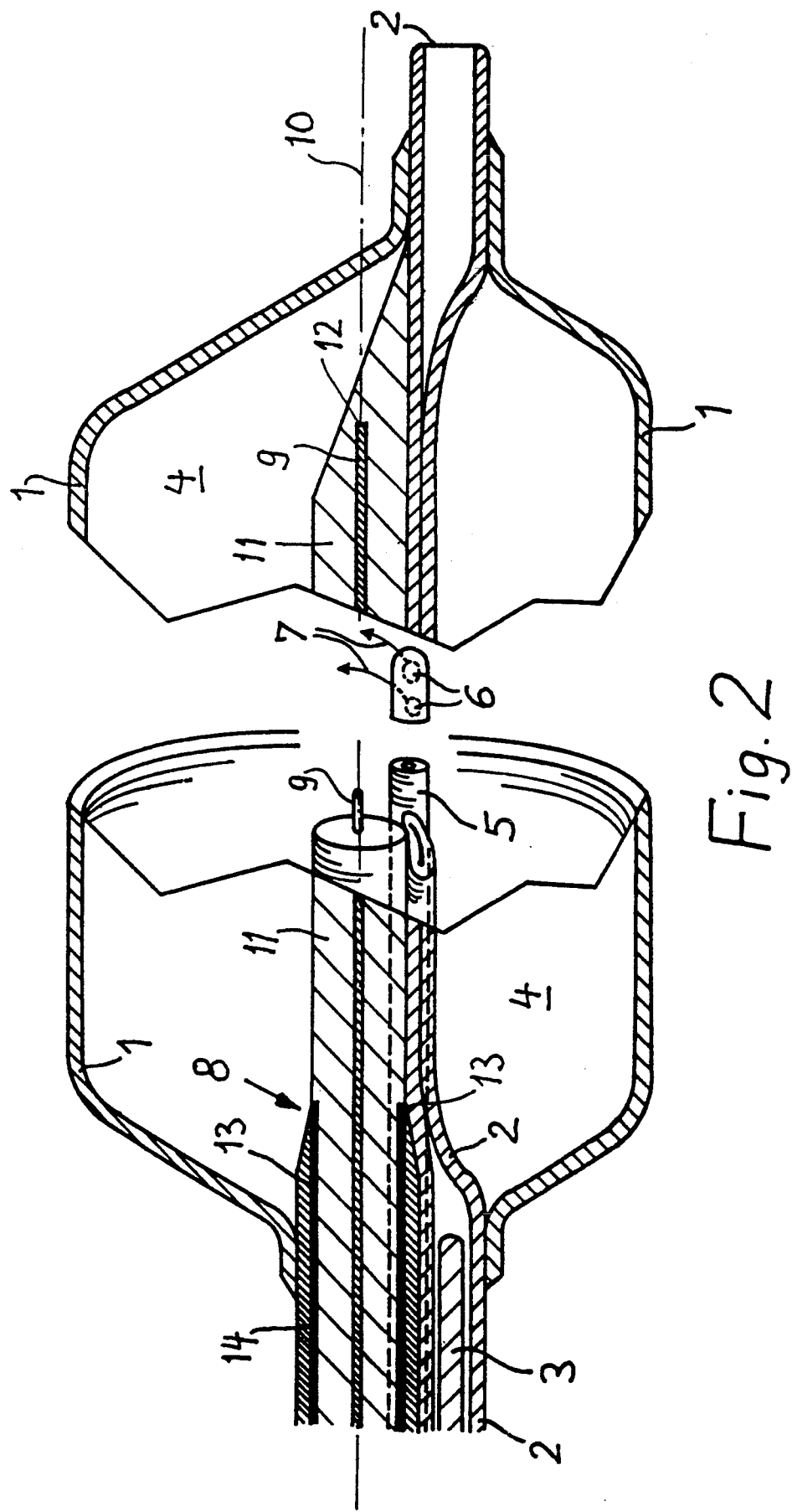
Figure 3:
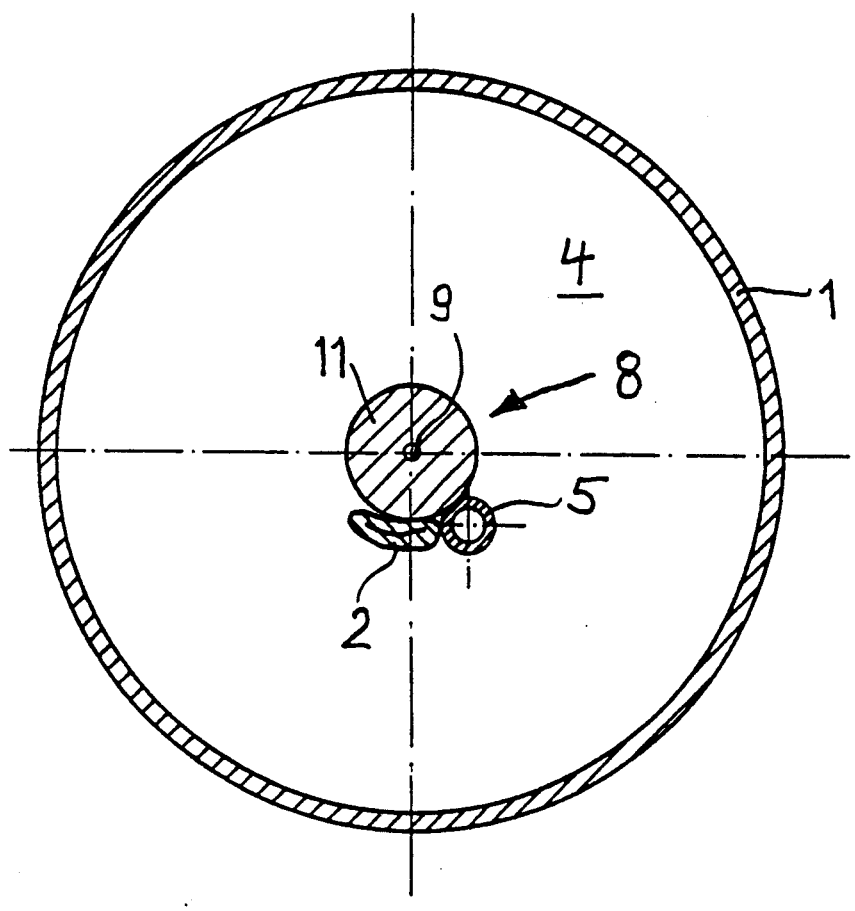

To inflate the envelope 1 with a fluid forced into the interior 4 of the envelope 1, an inflation tube 5 is provided, shown dotted in FIG. 1 and in partial perspective in FIG. 2. The inflation tube 5 has orifices 6 at its anterior end, through which communication is set up between the interior of the inflation tube 5 and the interior 4 of the envelope 1, so that the liquid can be forced into the interior 4 of the envelope 1 as indicated by arrows 7.

When the envelope 1 of the balloon catheter is located in the region of a stenosis to be rechanneled in a coronary vessel of the patient, the guide wire 3 is retracted more or less to the position seen in FIG. 2.

As may be seen in FIG. 2, the guide hose is long enough at the end to the left in FIGS. 1 and 2 to prevent the guide wire 3 from escaping out of engagement with the guide hose 2 when retracted.

When the interior 4 of the envelope 1 is charged with liquid under pressure as shown in FIGS. 2 and 3, the guide hose 2 is squeezed flat by the internal pressure in the manner indicated in the envelope 1 in FIGS. 2 and 3, with the result that no heat-coagulated blood will pass through the guide hose 2 in the direction towards the retracted guide wire 3.

Above the guide hose 2 and inflation tube 5 in FIGS. 1, 2 and 3, a coaxial cable 8 is seen. The metallic inner conductor 9 of the coaxial cable 8 extends along the centerline 10 drawn in FIGS. 1 and 2 into the vicinity of the envelope 1, but leaving a distance between the anterior end of the inner conductor 9 shown at the right in FIGS. 1 and 2 and the inflated envelope 1.

The inner conductor 9 of the coaxial cable 8 is sheathed with insulation 11, likewise electrically insulating the anterior end 12 of the inner conductor 9 from the liquid for example present in the interior 4.

The shielding 13 of the coaxial cable 8 extends by an amount more or less matching the distance of the anterior end 12 of the metallic inner conductor 9 from the envelope 1 into the interior 4 of the envelope 1. As usual for coaxial cables, the shielding 13 of the coaxial cable 8 is enclosed by an outer protective jacket 14. The coaxial cable 8 extends together with the guide wire 3 and the inflation tube 5 through a guide catheter not shown in the drawing, terminating for example in the inguinal region of the patient's body, to a microwave generator with a frequency in the range from 400 MHz to 10 GHz. The output power and the on-times of the microwave generator are preadjustable, a pressure switch not shown in the drawing preferably sensing the internal pressure in the envelope 1 in order to permit the microwave generator to be switched on only at a dilatation pressure at which the guide tube 2 is squeezed flat, thus securely avoiding any coagulation of blood by the microwaves in the guide hose 2. Specifically, the microwave generator may be so constructed that the high-frequency output is made available pulsewise, the pulse test ratio and the duration of a pulse train being preadjustable according to the prevailing conditions of operation.

When the envelope 1 has taken on the more or less cylindrical shape represented in FIGS. 2 and 3 and the inner conductor 9 lies along the centerline of the vessel to be dilated, the microwave generator is switched on and the liquid is heated as a heat reservoir around the inner conductor 9 acting as antenna and then the inner vessel wall is heated by conduction to perform a thermal aftertreatment of the mechanically dilated vessel wall, in particular a vessel wall coagulation, thus reducing the tension set up in the vessel wall and/or coagulating any existing lesions. The heating of the liquid is accomplished by absorption of microwave energy. To increase absorption, it is expedient for the liquid used to be a common salt solution that may be mixed with an X-ray contrast medium containing iodine. In addition, metal particles or other substances absorbing microwaves may be mixed in.

The zone of thermal influence may be adapted to prevailing conditions by choice of liquid medium and the frequency, power and pulse shape of the microwaves. Adaptation is possible also by means of the aforementioned metallic coating on the envelope 1. Depending on choice of liquid and form of coating, the latter may merely shield the envelope 1 or be itself heated and give off its own heat or heat transferred from the liquid to the surroundings by conduction.

After the thermal treatment, the envelope 1 is decompressed and the balloon catheter is retracted together with the guide wire 3.

Retraction of the guide wire 3 before the microwave generator is switched off also has the result that the microwave output emerging in the unshielded region of the inner conductor 9 will not be shielded by the guide wire 3, and in particular the guide wire 3 will not be heated.

The envelope 1 is welded to the guide hose 2 at the end on the right in FIGS. 1 and 2. At the posterior end, shown on the left in FIGS. 1 and 2, the envelope 1 is welded tight to the guide hose 2 and the outer jacket 14 of the coaxial cable 8.

In the balloon catheter to be heated with microwaves as described above, energy is introduced into the balloon and there converted into heat in the liquid and/or the coating of the envelope without passing a current through the body of the patient and without presence of a galvanically closed circuit.

The balloon catheter may be employed to especial advantage in coronary vessels. Alternatively, however, with suitably enlarged diameter, it may be used to dilate other arterial vessels as well as any body passages and cavities.

I claim:

1. A balloon catheter for rechanneling stenoses in body passages, in particular of coronary and peripheral arterial vessels, said catheter comprising a balloon having an interior through which a guide hose to be guided by a guide wire extends, said balloon including an inflation tube opening into the interior of the balloon, wherein a microwave antenna is located, said antenna coupled to a coaxial cable, the balloon including means for absorbing and/or shielding microwave radiation, and further wherein the guide hose consists of a readily deformable material and hence can be clamped off upon inflation of the balloon.

2. A balloon catheter of claim 1 including a pressure sensor means for generating a signal when the internal balloon pressure exceeds a predetermined threshold, whereby the microwave generator is controllable so as to be switched on only at sufficient pressure to squeeze the guide hose flat.

* * * * *